United States Patent [19]

Neuendorf et al.

[11] 4,200,798
[45] Apr. 29, 1980

[54] DENTAL X-RAY DIAGNOSTIC APPARATUS

[75] Inventors: Manfred Neuendorf, Lorsch; Ernst Schmitt, Bensheim; Gustav Schubert, Lorsch, all of Fed. Rep. of Germany

[73] Assignee: Siemens Aktiengesellschaft, Berlin & Munich, Fed. Rep. of Germany

[21] Appl. No.: 967,363

[22] Filed: Dec. 7, 1978

[30] Foreign Application Priority Data

Dec. 27, 1977 [DE] Fed. Rep. of Germany ....... 2758191

[51] Int. Cl.$^2$ ............................................. G03B 41/16
[52] U.S. Cl. .............................. 250/439 P; 250/416 R
[58] Field of Search .............. 250/439 P, 439 R, 444, 250/445 R, 446, 447, 448, 449, 451, 456, 490, 491, 402, 416 R

[56] References Cited

U.S. PATENT DOCUMENTS

| 4,002,915 | 1/1977 | Weiss | 250/439 P |
| 4,145,611 | 3/1979 | Valila | 250/439 P |

Primary Examiner—Craig E. Church
Attorney, Agent, or Firm—Hill, Van Santen, Steadman, Chiara & Simpson

[57] ABSTRACT

In an exemplary embodiment a unit which can be rotated about vertical axes, essentially comprises an x-ray tube and a film carrier, with a head support arranged therebetween and used for the support of a patient's head. The head support is adjustably arranged in a horizontal plane relative to a mounting therefor so the head can be held in various positions for various object exposures. The adjustable positions are marked on an index field according to the different object exposures and can be selected by means of position selectors. A scanning device having signal indicators is coupled to the position selectors so that the position of the head support relative to its mounting is determined, and so that when the selected position is reached, a signal activates a display element assigned to the respective actuated position selector and arranged in the index field (FIG. 3).

9 Claims, 4 Drawing Figures

U.S. Patent  Apr. 29, 1980  Sheet 1 of 2  4,200,798
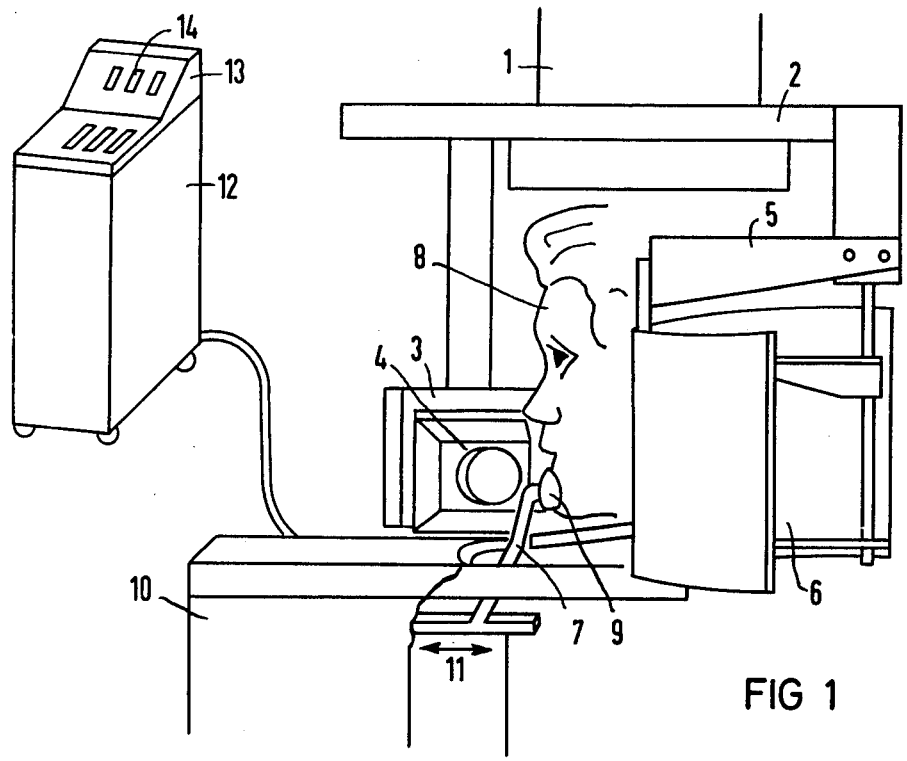
FIG 1
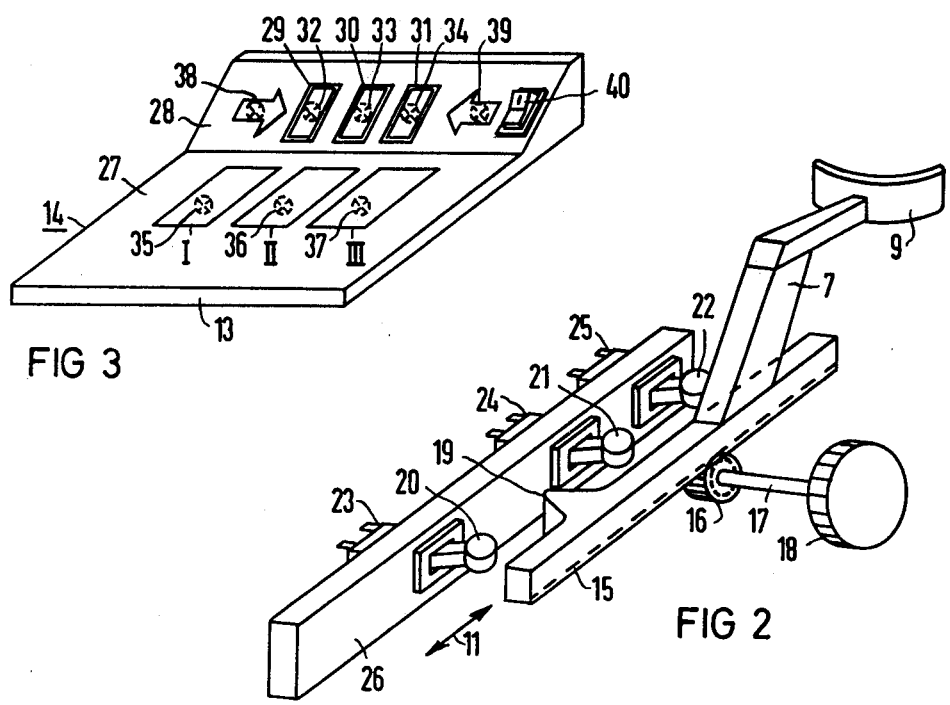
FIG 3
FIG 2

DENTAL X-RAY DIAGNOSTIC APPARATUS

BACKGROUND OF THE INVENTION

The invention relates to a dental x-ray diagnostic apparatus having a unit which can be rotated about vertical axes, essentially comprising an x-ray tube and a film carrier, and having a head support arranged therebetween for the support of the patient's head, said head support being adjustably arranged in a horizontal plane vis-a-vis its mounting in order to provide the possibility of locating the head in various positions for different object exposures.

In order to do justice to various exposure techniques in the mandible region of a patient in dental x-ray diagnostics; for example, in order to make exposures of the quadrant tooth sector, of the sinus cavities, the mandible joints or ear passages, it is necessary to adjust a head support, which can be outfitted with a chin support, a bite block or with a front tooth support, to various positions, at least in the horizontal plane.

In known dental x-ray diagnostic apparatus a pointer is attached at the head support, which is adjustably attached on a guide rail, which pointer cooperates with a line scale arranged on the mounting. The respectively adjusted position of the head support can be read on the line scale.

With the adjustment of the various positions it can easily happen that the pointer is accidentally set for a wrong scale value, and thereby the head support is not adjusted in the respective position for the desired exposure. Moreover, the searching for the respective scale value for a desired exposure is relatively time-consuming.

SUMMARY OF THE INVENTION

In contrast thereto it is the invention's objective to provide an improved x-ray diagnostic apparatus facilitating an easier and more reliable adjustment of the head support to the positions which are necessary for the respective exposure technique.

The objective strived for in a dental x-ray diagnostic apparatus of the initially mentioned type according to the invention is obtained in that the adjustable positions of the head support are marked on an index field according to the various object exposures, that each position can be selected by means of a position selector arranged in the index field, and that a scanning device with signal indicators is coupled to the position selectors, by means of which scanning device the position of the head support relative to its support is determined and which supplies a signal to an indicator element assigned to the respective position selector and arranged in the index field.

Advantageous embodiments and further developments are contained in the subclaims.

One inventive sample embodiment is hereafter more precisely explained with the aid of the accompanying sheets of drawings; and other objects, features and advantages will be apparent from this detailed disclosure and from the appended claims.

BRIEF DESCRIPTION OF THE DRAWINGS

FIG. 1 illustrates the essential parts of a dental x-ray diagnostic apparatus in a diagrammatic view;

FIGS. 2 and 3 illustrate details of the apparatus shown in FIG. 1; and

DETAILED DESCRIPTION

Figure 4:
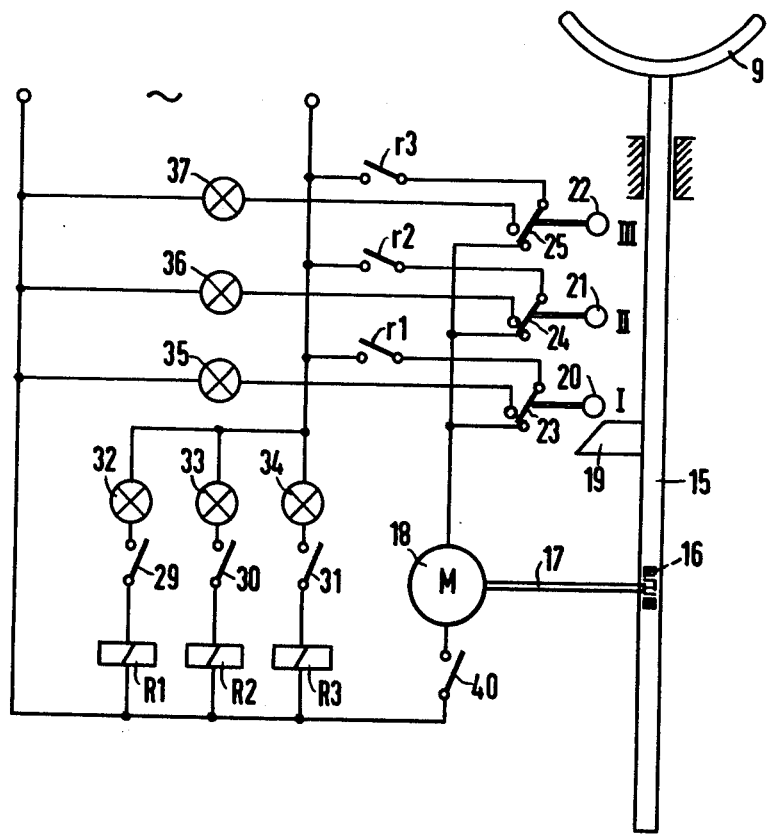
FIG. 4 illustrates a basic circuit diagram for disclosing the positioning means for the head support in principle.

FIG. 1 illustrates the essential components of a dental x-ray diagnostic apparatus in a diagrammatic overview illustration, as they are used for overview exposures in the dental-mandible field. The apparatus essentially consists of a carrying device 2, rotatably supported by a carrying column 1, for a first carrying arm 3, with which an x-ray tube 4 is supported, and an additional carrying arm 5, with which an arc-shaped curved film carrier 6 is supported. A head support 7 is located between the film carrier 6 and the x-ray tube 4 for the support or rest of the patient's head 8. The head support 7 in the present sample embodiment is equipped with a chin support 9; or with a bite block which is inserted into the patient's mouth or a front tooth support either of which can be provided on the head support 7 (FIG. 2) in place of the chin support 9.

For producing a tooth-or mandible exposure, the head 8 of the patient is positioned in the head support 7. For better overview's sake, additional necessary perhaps for the positioning and adjusting of the head are not drawn here. Whereas the x-ray tube 4 and the film carrier 6 rotate about the patient's head 8 according to a rotating system, not more precisely explained but understood in the art, the patient's head must be rigidly supported by the head support during the exposure.

In order to comply with various exposure techniques, for example, in order to be able to make quadrant tooth sector-, sinus-cavity-, mandible joint- or ear tract exposures, it is necessary to bring the patient's head 8 into various positions in the extension of the lamino-arch axis. The head support 7 is therefor adjustably mounted on a mounting in a housing, referenced 10, and has an axis of adjustment parallel to the direction of the arrow 11.

A mobile unit is referenced 12, which contains the necessary electric equipment for the operation of the x-ray diagnostic apparatus. A console section 13 is mounted on the cover of the unit 12, and has an index field 14 equipped with various marking and display elements.

FIG. 2 illustrates details concerning the design and the mounting of head support 7. Head support 7 exhibits a toothed rack 15 meshing with a gear wheel 16 driven by a drive 18 (hand wheel or motor drive) via an axis 17. The rack 15 exhibits a contact cam 19, which activates levers 20 through 22 in succession when the rack is advanced parallel to the direction of arrow 11. The levers cooperate with microswitches 23 through 25, which are arranged at a specific spacing on a support 26, such spacing corresponding with the required patient's head positioning for the respective exposure.

FIG. 3 shows details of the console section 13. Console 13 exhibits a segment 27, essentially extending horizontally, and a segment 28 running obliquely thereto. Three adjustable patient's head positionings I, II, III are marked in segment 27. The marking I, for example, can symbolize a normal exposure, marking II a sinus cavity exposure, and III a mandible joint exposure. Position selectors 29 through 31 in the form of switches are assigned to the respective exposure positions of the head support 7 corresponding with markings I through III. The selector switches 29 through 31 are optically emphasized by display lights 32 through 34, respectively, as will be more precisely explained later. The patient positioning markings I through III also exhibit display lamps 35 through 37, which light up when the position, preselected by the position selectors 29 through 31, is attained. The numerals 38 and 39 reference two luminous arrows indicating the motion direction of head support 7 during an adjustment. The electrical equipment is switched on by main switch 40.

From FIG. 4, illustrating a simple basic circuit diagram of the equipment, can be concluded that after activating one of the position selectors 29 through 31 the respective display lamp 32 through 34 lights up. Simultaneously a respective one of relays $R_1$, $R_2$ or $R_3$ is energized to close contacts $r_1$, $r_2$ or $r_3$. Assumedly, the main switch 40 is switched on, so that the drive motor 18 is energized via the actuated relay contacts and the rack 15 is moved in an axial direction. When the patient position for the respective switch-on position selector is obtained, the corresponding patient positioning display lamp 35, 36 or 37 lights up to illuminate the associated marking I, II or III of console segment 27, FIG. 3. The marking regions I, II and III may contain visual indicia or graphical symbols representing the respective associated exposure techniques and corresponding to the respective head support position I, II or III of FIG. 4. The operator thereby receives the information that the head support is in the correct position according to the exposure technique selected. Simultaneously, the switching-off of drive 18 proceeds via switch 23, 24 or 25.

A purely optical scanning device with the aid of lamps and photo-resistors, which actuate the display lamps in index field 14 in the manner described, can also be provided in place of cam 19 in conjunction with the microswitches 23 through 25. The current supply for both variants expediently proceeds with low voltage (AC or DC voltage).

In the basic circuit diagram according to FIG. 4, the control components, necessary for the rotation direction reversal of the drive, in particular the holding- and locking control components, are not drawn in for a better overview.

It will be apparent that many modifications and variations may be effected without departing from the scope of the novel concepts and teachings of the present invention.

We claim as our invention:

1. A dental x-ray diagnostic apparatus having a unit which can be rotated about vertical axes, essentially comprising an x-ray tube and a film carrier, and a head support arranged therebetween used for the support of the patient's head, said head support being adjustably arranged in a horizontal plane relative to a mounting therefor in order to provide a better positioning for various object exposures in different positions, characterized in that position selectors (29 through 31) for respective adjustable positions (I, II, III) of the head support (7) have respective display elements (35 through 37), an index field (14) being marked (at I, II, III, FIG. 3) according to the various object exposures, that each position can be selected by a respective corresponding position selector (29 through 31) arranged in the index field (14), and that a scanning means (19 through 25) having signal indicators (23, 24, 25) is coupled with the position selectors (29, 30, 31) for automatically positioning the head support (7) relative to its mounting (10) and for supplying a signal to a respective display element (35 through 37) arranged in the index field (14) and assigned to the respective position selector (29 through 31) when the selected position is reached.

2. An x-ray diagnostic apparatus according to claim 1, characterized in that the scanning means (19 through 25) comprises a movable actuator (19) controlling electric switches (23 through 25) forming the signal indicators.

3. An x-ray diagnostic apparatus according to claim 2, characterized in that the movable actuator essentially comprises a contact cam (19) arranged on a rod (15) carrying the head support (7), and the scanning means having switch levers (20 through 22) responsive to movement of the contact cam (19) and cooperating with electric switches in the form of microswitches (23 through 25).

4. An x-ray diagnostic apparatus according to claim 3, characterized in that the rod comprises a toothed rack (15) carrying the head support (7) and adjusted via a gear wheel (16) which is driven by hand or by an electric motor.

5. An x-ray diagnostic apparatus according to claim 1, characterized in that the index field (14) has markings for representing the adjustable positions which exhibit optical display elements (35 through 37).

6. An x-ray diagnostic apparatus according to claim 5, characterized in that the position selectors (29 through 31) also contain optical display elements (32 through 34) which responds when the associated position selector is activated.

7. An x-ray diagnostic apparatus according to claim 1, characterized in that the index field (14) is arranged at the upper side of a console housing (13).

8. An x-ray diagnostic apparatus according to claim 7, characterized in that the console housing (13) exhibits a horizontal panel (27) in which the markings representing the individual positions are arranged, and an obliquely extending panel (28) with the position selectors (29 through 31) arranged therein.

9. An x-ray diagnostic apparatus according to claim 1, characterized in that light arrows (38, 39) are arranged in the index field (14), said light arrows being respectively energized to indicate the respective motion direction of the head support (7) during the adjustment.

* * * * *